United States Patent [19]

Beutel

[11] Patent Number: 5,866,334
[45] Date of Patent: Feb. 2, 1999

[54] DETERMINATION AND IDENTIFICATION OF ACTIVE COMPOUNDS IN A COMPOUND LIBRARY

[75] Inventor: Bruce A. Beutel, Suffern, N.Y.

[73] Assignee: Genzyme Corporation, Framingham, Mass.

[21] Appl. No.: 683,108

[22] Filed: Jul. 16, 1996

Related U.S. Application Data

[63] Continuation of Ser. No. 223,519, Apr. 5, 1994, abandoned.

[51] Int. Cl.$^6$ .............................. C12Q 1/68; C07K 1/22
[52] U.S. Cl. .............................. 435/6; 435/962; 530/412
[58] Field of Search .................... 435/6.962; 530/412

[56] References Cited

U.S. PATENT DOCUMENTS

| | | | |
|---|---|---|---|
| 5,002,867 | 3/1991 | Macevicz | 435/6 |
| 5,270,163 | 12/1993 | Gold et al. | 435/6 |

FOREIGN PATENT DOCUMENTS

| | | | |
|---|---|---|---|
| 9305182 | 3/1993 | WIPO | 435/6 |

OTHER PUBLICATIONS

Needels et al., PNAS, USA 90: 10700–10704 (Nov. 1993).
Houghten et al. Biotechniques 13(3): 412–421 (1992).
Houghten et al. Nature 354: 84–86 (Nov. 7, 1991).
Oliphant, et al., *Mol. Cell. Biol.*, vol. 9, No. 7, pp. 2944–2949 (1989).
Ecker, et al., *Nucl. Acids Res.*, vol. 21, No. 8, pp. 1853–1856 (Mar. 18, 1993).
Devlin, et al., *Sciences*, vol. 249, pp. 404–406 (Jul. 1990).
Brenner, et al., *Proc. Nat. Acad. Sci.*, vol 89, pp. 5381–5383 (Jun. 1992).
Lam, et al., *Nature*, vol 354, pp. 82–84 (Nov. 7, 1991).
Houghten, et al., *Nature*, vol. 354, pp. 84–86 (Nov. 7, 1991).
Houghten, *Gene*, vol. 137, pp. 7–11 (1991).
Pinilla, et al., *Gene*, vol. 128, pp. 71–76 (1993).
Bunin, et al., *J. Am Chem. Soc.*, pp. 10997–10998 (1992).
Tuerk & Gold, Science 249: 505–10 (3 Aug. 1990).

*Primary Examiner*—Stephanie W. Zitomer
*Attorney, Agent, or Firm*—Elliot M. Olstein; Raymond J. Lillie

[57] ABSTRACT

Libraries of compounds such as nucleic acids or peptides are contacted with a target molecule and libraries that have at least one compound that bind with at least a minimum activity are determined by a reiterative process in which a change in the rate of recovery (elimination) of compounds that bind to the target indicates that the library contains such a compound. The procedure may also be used to determine indirectly the sequence of such compound by employing sublibraries, each of which have a known entity at a known position of the compound.

12 Claims, 5 Drawing Sheets

DETERMINATION AND IDENTIFICATION OF ACTIVE COMPOUNDS IN A COMPOUND LIBRARY

This patent application is a continuation of patent application Ser. No. 08/223,579, filed Apr. 5, 1994, now abandoned.

BACKGROUND OF THE INVENTION

This invention relates to determining whether or not there is an active compound in a compound library. This invention further relates to determining the identity of an active compound present in a library of compounds.

Various procedures have been proposed for identifying compounds present in a library of compounds that are active with respect to a specified target. Such activities have generally been directed to identifying nucleic acids or peptides which bind to a protein or other target molecule.

For example, one such procedure for identifying a nucleic acid present in a nucleic acid library that binds to a target molecule involves contacting a library with a target molecule, by a reiterative procedure, which includes amplification. Thus, for example, Kinzler & Vogelstein (Nucleic Acids Res. 17, 3645, 1989) and Tuerk and Gold (Science 249, 505, 1990) have disclosed an in vitro procedure in which the nucleic acids in the library are exposed to target molecules under competitive binding conditions. Those nucleic acids capable of binding to the target molecule are recovered in preference to those that are not bound, and the recovered, active, nucleic acids are subjected to an amplification procedure such as the polymerase chain reaction (PCR). The amplified nucleic acids are re-exposed to target, isolated and then amplified once again. The value of the amplification step is that with each iteration of the procedure the target is exposed to a mixture of nucleic acids that is progressively enriched for molecules that bind with the highest affinity to the target. This is considered to be a combinatorial approach because it is the property of the entire active nucleic acid molecule that contributes to its ability to bind to the target and leads to its selection to the exclusion of other molecules in the library that bind to the target with lower affinity. The procedure avoids a signal (active nucleic acids) -to-noise (non-active nucleic acids) problem by its process of reiteration. Each time the library is exposed to the target in early iterations, the amount of bound highly active nucleic acids may be very small compared to the background of those bound or recovered that are not active, but eventually the active nucleic acids are abundant enough because of the reiteration and amplification that they can be easily measured and identified. For these reasons, very large libraries can be used and even single molecules of highly active members can be identified. The reiterative procedure, when taken as a whole and coupled with amplification, has a low enough background and eventually a high enough signal from active nucleic acids that it overcomes the usual limitations from signal-to-noise ratio that restrict the useful complexity of most screening procedures. While this is impressive, this class of procedures effectively and dramatically limits the chemical diversity allowed in the libraries. This essentially means that only nucleic acids or slightly modified nucleic acids can be used because these methods rely upon amplification and discrimination by biological methods in order to allow both completion of the reiteration as well as direct and accurate identification of the active members of the library at the end of the procedure.

Screening procedures for peptide libraries are not reiterative. In vitro techniques such as PCR that will amplify peptides are not currently available. Accordingly, different strategies have been implemented. In one such approach, peptides of random sequence are displayed on bacteriophage, the phage are contacted with a target and those phage that interact with the target are isolated, recloned and the sequences encoding the active peptides are determined (Devlin et al., Science 249, 404, 1990; Scott and Smith, Science 249, 386, 1990). In another approach, referred to by some as "Encoded Synthetic Libraries" (ESL), (Dower et al., Patent WO 93/06121; Brenner & Lerner, Proc. Natl. Acad. Sci., U.S. 89, 5381, 1992; Needels et al., Proc. Natl. Acad Sci. U.S. 90, 10700, 1993) peptides are bound either directly or via a bead to nucleic acids in such a way that as an amino acid is added to a growing peptide, one or more nucleotides encoding the added amino acid is added orthogonally to the bead or to the peptide. The advantage of the ESL approach is that high complexity synthetic peptide libraries can be assayed in a combinatorial fashion. All screening strategies that use codes to indirectly identify the active members of a library (such screens have been described for other kinds of synthetic libraries in addition to peptides) are designed to allow combinatorial selection of libraries to identify rare, highly active library members. The signal-to-noise problem is overcome by brute-force approaches such as using cell sorting technology to examine individual beads each containing multiple copies of a single library member and its corresponding code. In this sense, such procedures are, in effect, methods for quickly screening large numbers of compounds, one by one, with advanced technology, as opposed to screening pools or mixtures simultaneously. The coding technology facilitates the identification of the active compounds because in such methods the amount of material isolated is usually very small (i.e., one "bead's worth" of peptide). By using an amplifiable nucleic acid code, the direct identification of the code (and, therefore, the indirect identification of the active compound) is possible. There are, however, limitations to these kinds of technologies, including (1) the need for complex chemistry to couple the library members to their respective codes, (2) the need in some embodiments to have the peptides attached to a comparatively large bead which, even though it might be relatively inert, might nevertheless impede interaction between peptide and target, (3) possible interaction between the target and the nucleic acid code or between peptides and codes and (4) in some of these procedures the compounds of the library are not in solution so that the selection conditions are dissimilar from those in which an active compound would normally be expected to function, namely binding in solution to the target.

There are serial approaches for screening peptide libraries (Houghten et al., Nature 354, 84, 1991) that do not have the complications of encoded library methodologies. Typically, a library consists of pools of peptides each containing the same number of amino acids; for example, the library might contain 400 pools of hexameric peptides such that each pool has one of the 20 amino acids in the first and second position of the peptides (thus 20×20=400 pools) and the remaining 4 positions of the peptides are random in every pool. The target is contacted with each of the 400 pools and each pool is measured for activity; for every active pool (for example, ala.his.x.x.x.x), 20 new sub-pools are synthesized wherein the first two amino acids of the active pool are conserved (i.e., ala.his), the third amino acid is fixed (i.e., ala.his.gly.x.x.x in the first pool, ala.his.ala.x.x.x in the second pool and so on) and the fourth, fifth and sixth positions are randomized so that the 20 pools are distinguished by the identity of the amino acid in the third position of the peptide. This serial "unrandomization" procedure is continued until active peptides have been selected in which all six positions are identified. Such a procedure has also been described for oligonucleotides (Ecker et al., patent WO93/04204). This kind of procedure avoids the chemical limitations of the oligonucleotide procedures that use amplification (i.e., the library members do not need to be amplified), as well as the chemical complications of the encoded-library procedures, but these limitations are replaced by the signal-to-noise problem because these procedures are essentially no more than serial pooling strategies that do not effectively address the signal-to-noise limitation. Therefore, these approaches are additive rather than combinatorial, whereby pools containing less active but more abundant subclasses of compounds will be chosen whereas pools containing less abundant, more active compounds are likely to be ignored. Thus, in the example given above, the pool with the best average activity might have been ala.his.x.x.x.x but there might have been individual members in other pools (e.g., val.leu.x.x.x.x) that had higher activity than any individual members in the selected pool but these would not be identified.

In summary, there are three common kinds of procedures for screening synthetic libraries: (1) For oligonucleotides, there are reiterative procedures that include amplification of the nucleic acids. These procedures are combinatorial and minimize the signal-to-noise problem. Without amplification, the direct identification of the active compounds present in large libraries by these procedures would not be possible because the amount of material recovered from the reiterative procedure would be too low to use in known procedures for identifying nucleic acid sequences. Because of the requirement for amplification, however, these procedures are restricted to a very limited set of compounds, namely nucleic acids that can be amplified. (2) Coding procedures are used to facilitate identification of non-amplifiable compounds via amplification of nucleic acid codes that are associated with, or bound to, each compound of a library. These procedures are combinatorial to the extent that the signal-to-noise problem is reduced by the use of screening procedures that minimize the noise and maximize the signal generated by even a single active library member. Such procedures, which usually involve physical separation of a solid support to recover copies of those individual compounds that are active, result in low yields of material, but the amplification of the code allows direct identification by known methods of nucleic acid sequencing. These procedures are generally more cumbersome, do not allow sampling in solution phase, and present challenges in chemistry that stem from the need to have a unique nucleic acid code attached to each compound in the library. (3) Serial "unrandomization" procedures are used to screen synthetic libraries for active compounds. These procedures are very flexible with regard to the chemistry that can be used and avoid some of the complications of the other procedures, but they are not combinatorial because they do not address the signal-to-noise problem. Therefore, procedures (1) and (2) limit the kinds of libraries that can be screened for technical (chemistry) reasons, whereas procedure (3) is likely to yield relatively abundant, less active compounds in preference to the rarer, most active compounds. A procedure that would enable the use of a wide variety of chemistries and synthetic libraries in solution, as in procedure (3), but that was also truly combinatorial, effectively minimizing or eliminating the signal-to-noise problem, as in procedures (1) and (2), would be a very powerful screening approach. The invention described below is a description of one such procedure.

SUMMARY OF THE INVENTION

In accordance with one aspect of the present invention, there is provided a procedure for determining whether or not there is present in a library of compounds an active compound.

In accordance with another aspect of the present invention, there is provided a procedure of identifying an active compound which is present in a library of such compounds.

In accordance with a further aspect of the present invention, there is provided a procedure which is applicable to a wide variety of different compounds, and which does not require amplification, and which is capable of distinguishing between those libraries that contain a unique or very rare compound(s) having at least a desired activity and those libraries that include a high representation of compounds with some lower level(s) of activity.

The present invention also provides an indirect method for identifying the compound or compounds present in a library which has a specified activity for a target molecule.

DESCRIPTION OF DRAWINGS

The present invention will be further described with respect to the Drawings wherein.

DETAILED DESCRIPTION OF THE INVENTION

Figure 1:
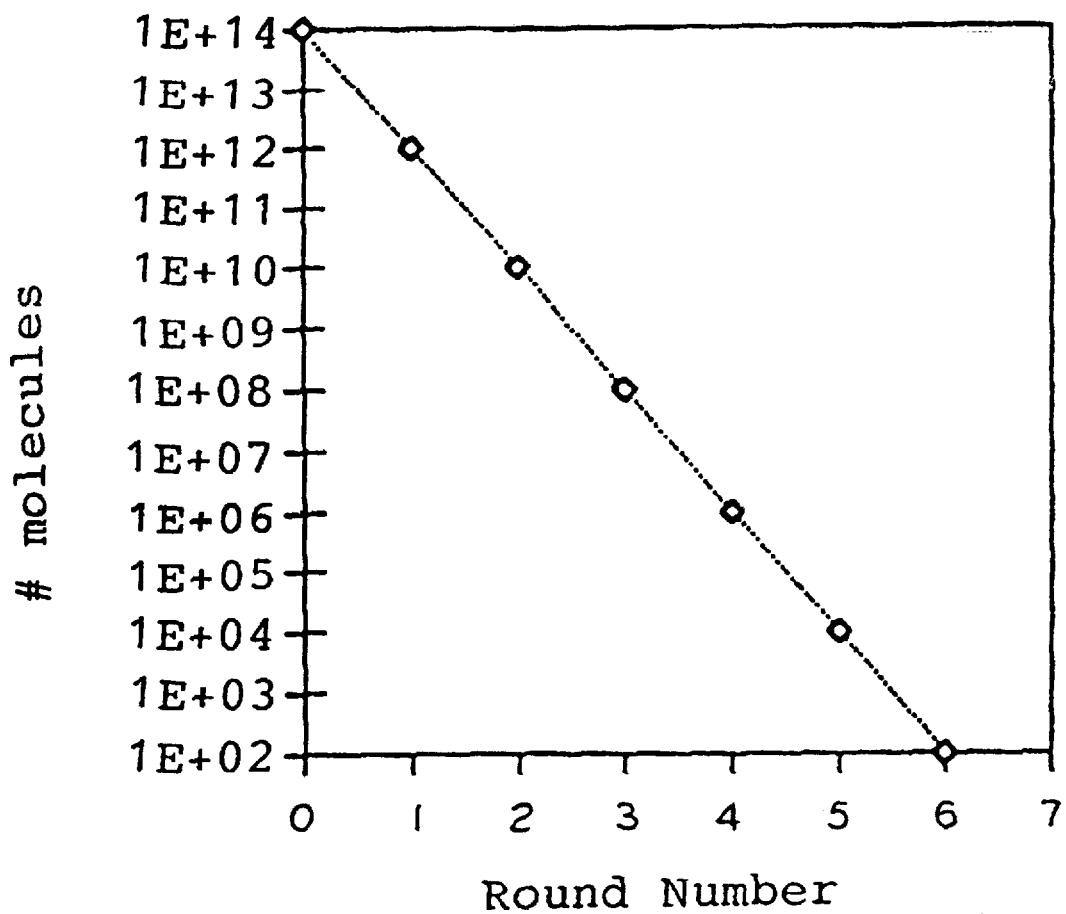
FIG. 1 graphically represents changes in recovery for each round in a reiterative process for a library containing only "losers"

More particularly, in accordance with an aspect of the present invention, there is provided a process for screening a library of compounds to determine whether or not there is present in such library at least one compound (hereinafter referred to as a "winner") that binds to a target molecule with at least a specified level of affinity, $K_d$ (dissociation constant) or activity wherein the library is contacted with a target molecule under conditions at which those compounds present in the library having at least the specified level of activity bind to the target molecule. As a result of such contacting, there is bound to the target any compounds which have the specified level of activity in admixture with compounds which do not have such activity. Thereafter, those compounds having less than the specified level of affinity or activity (hereinafter referred to as "losers") are eliminated from the mixture at a faster rate than winner compounds. The presence in the library of at least one winner compound is determined by detecting a change in the rate at which compounds are eliminated (recovered) from the mixture (which can be detected by either measuring elimination of compounds or measuring recovery of compounds), with such change in rate being reflected as a change in the percentage of the compounds eliminated (recovered) during such elimination (recovery).

Thus, for example, if there is to be determined whether or not a library contains a winner compound or compounds which bind to a target molecule with at least a specified affinity (or $K_d$), the library is contacted with the target molecules under conditions appropriate to recover by partitioning from the library winner compounds that are bound to the target. Under such conditions, some loser compounds will also be recovered. The recovery of such loser compounds can be due to the background in the assay and/or binding of abundant compounds with low activity. Upon repeating of the procedure wherein compounds recovered in the first contacting are again contacted with the target, losers will be eliminated at a faster rate than winners. Thus, the proportion of winners to losers increases rapidly with each iteration of exposure to target. At some point in the reiteration process, the proportion of winners to losers becomes great enough that winner compounds predominate in the population. Accordingly, if one plots recovery of total compounds per round of iteration, there is a decrease in the rate of elimination of compounds, and ultimately, in an idealized situation, a plateau is reached and the amount of compound observed binding to target with further iterations is constant. The presence of winner(s) in a library can be readily detected by determining a change in the rate of the elimination of the compounds that bind to the target, or a change in the rate of recovery of unbound compounds from the mixture.

For example, suppose library C has 1000 copies of 1000 unique compounds, wherein all compounds are losers except compounds #C1-100, which have a $K_d$ for the target of 1 micromolar, and compound #C101, which has a 0.1 micromolar $K_d$ and is therefore ten times more active than any other compound in the library. Upon exposure of 0.1 micromolar target to the library in the first round of a reiterative procedure, 50%, or about 500 copies, of #C101 will be recovered (because the target concentration is equal to $K_d$ for this compound) whereas only about 10%, or 100 copies of #C1-100 will be recovered. In addition, suppose that the recovery procedure has a background recovery of 1%, or about 10 copies of the other 899 compounds (#C102-1000). In the second round of reiteration, 50% of the remaining #C101, or about 250 copies, are recovered along with 10%, or 10 copies, of #C1-100, and 1% or a random assortment of about 90 of the inactive compounds. To summarize, after two rounds there are 250 copies of #C101, 10 copies of the 100 less active compounds #C1-100, and 90 unique inactive compounds. After a third round, there would be about 125 copies of #C101, only one copy of each of the 100 less active compounds, and virtually no loser compounds recovered. #C101 would now be in a majority in the remaining library even though originally it was outnumbered 100:1 by compounds that were only 10 times less active.

Thus, the predominance of compound C101 would result in a change in the rate of elimination of the compounds (or a change in the rate of recovery of the compounds) in subsequent iterations, and such change in the rate of recovery or rate of elimination indicates that the library contains a compound that has at least the specified activity (a winner).

The present invention takes account of the fact that if a library contains rare compounds that interact specifically with a target, after contacting said library with target and isolating active compounds, some small percentage of inactive compounds, or compounds with lower activity, will also be isolated. The recovery of inactive compounds can be due to the background in the assay and/or the binding of abundant compounds with low activity. When the process of contacting compounds with target and isolating active compounds is reiterated, the same small percentage of inactive or less active compounds will be recovered with the most active compounds. Because the percentage recovery of most active compounds will be much greater than the percentage recovery of inactive or less active compounds per round, there will be an ever widening difference in the cumulative percentage of active and inactive compounds recovered through the reiterative procedure.

The underlying principle of the present invention is in the difference in signal between a library that contains a highly active compound and a library that does not. Suppose that library D is identical to library C in composition but does not contain a compound equivalent to #C101. That is, #D1-100 all have low activity with $K_d$=1 micromolar, and the other 900 compounds all have no activity (losers). Suppose libraries C and D were to be measured for "signal" (e.g. the remaining number of molecules) after each round. After the first round, library C would have about 500 copies of #C101, 100×100=10,000 of the less active #C1-100, and about 900×10=9000 losers for a total of 19,500 molecules. Library D would have 100×100=10,000 of #D1-100, and about 900×10=9000 inactive compounds for a total of 19,000 molecules. Note that library C has only 500 more molecules due to the highly active #C101. Measured as a percentage of the library put into the first round of reiteration, library C would have recovered 1.95% compared to 1.90% recovered for library D. This very small difference would very likely be within the experimental uncertainty (or "noise") of the binding and measurement methods. After two rounds, library C would have 250 copies of #C101, 100×10=1000 of #C1-100, and 89 of #C102-1000 for a total of 1,339 molecules compared to library D that would have 1089 molecules. The difference in recovery between the two rounds, more than 20%, might well be detectable. After round 3, however, library C would have 125 copies of #C101 and 100×1=100 of compounds #C1-100 for a total of 225 molecules, compared to library D that would only have 100×1=100 of compounds #D1-100. In other words, what was a minor difference in the first round, and a moderate difference in the second round, is now almost a 2-fold difference in percent recovery at round 3, with library C returning 225/1339, or nearly 17% recovery compared to library D returning 100/1089 or only about 9% of the input into the third round. This example underscores how a reiterative procedure can distinguish between two nearly identical libraries even when the difference between the two is only a single rare but highly active member.

Thus, it should be apparent from the above illustration that as compounds originally bound to the target are eliminated from library C, there is a detectable change in the rate of elimination or rate of recovery between rounds two and three for library C which has a winner, whereas in library D there is not a significant change in the rate of elimination or recovery of such compounds. Thus, whether or not a library contains a winner can be determined without amplification by detecting a change in the rate of elimination of those compounds that originally bound to the target.

As a further illustration of the process of the present invention for identifying whether or not a library contains a compound that binds to a target with at least a specified activity, there may be defined as a winner, a compound in the library that binds to a target with a $K_d$ value in the nanomolar range or less, whereas losers might bind to the target with a $K_d$ in the micromolar range or higher.

The binding of losers is commonly referred to as "nonspecific" because it is a characteristic shared by all library members. If a target can recognize and bind to a particular member or subclass (winners) with much higher affinity, such binding is referred to as "specific" because it is specific to those winners rather than to the other members of the library. For example, DNA-binding proteins typically have nonspecific binding affinity for any DNA sequence in the micromolar range whereas they bind specific DNA sequences with nanomolar or lower $K_d$.

If a library containing $10^{14}$ molecules contains no winners, it will have a low background value if appropriate conditions are chosen for assay. For example, in an appropriately designed binding assay, generally a total of 1% or less of losers is measured as interacting with the target. If a library containing only losers has a background value of 1% and those compounds associated with the target are recovered and re-exposed to target, once again only 1% of the compounds will be associated with target. Thus, if one were to continue this process of recovery of those compounds associated with target and re-exposure to target and to plot the results, one would predict a linear result in a semi-log plot as shown in FIG. 1.

Figure 2:
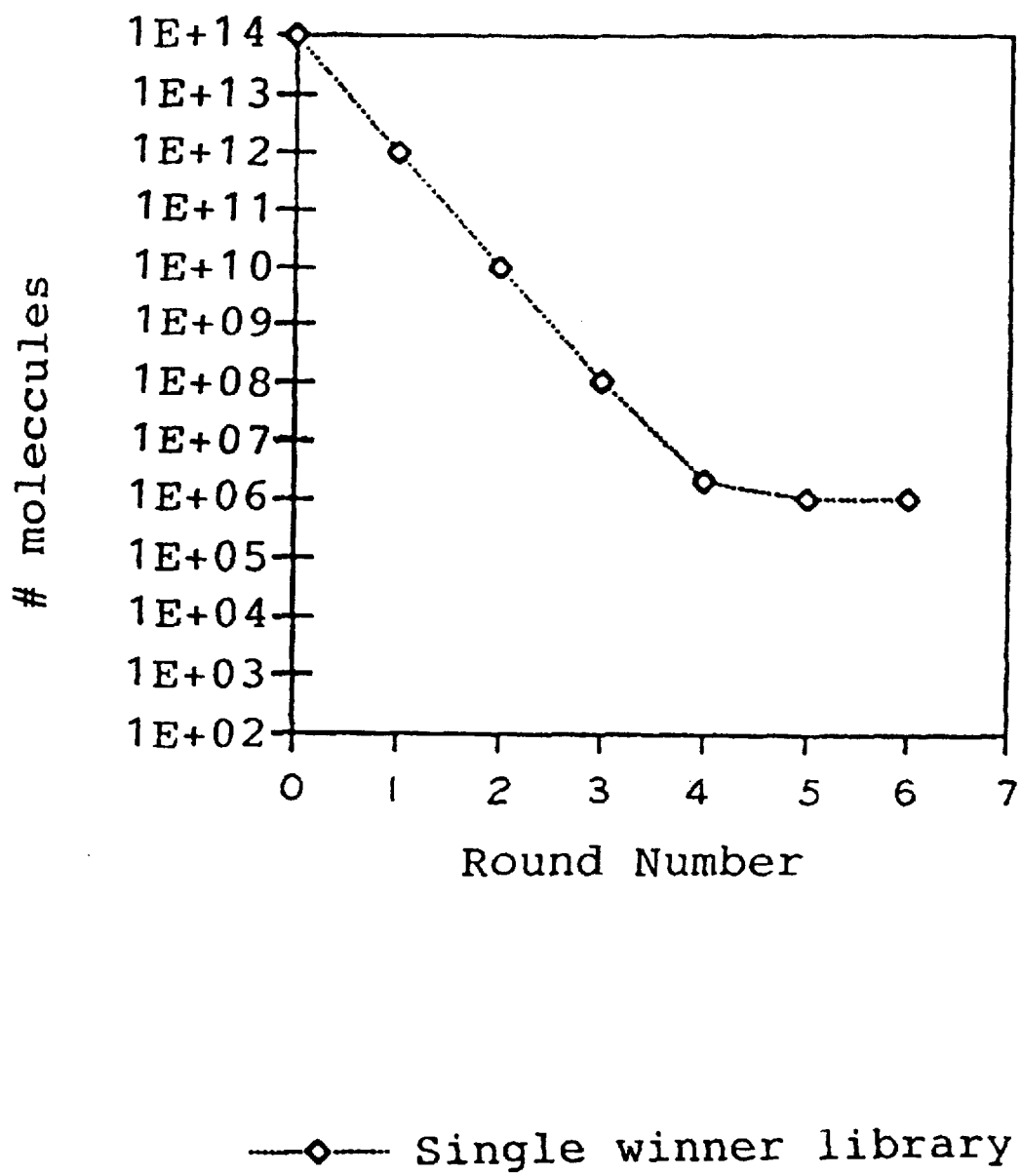
FIG. 2 graphically represents changes in recovery for each round in a reiterative process for a library containing a single "winner"
Figure 3:
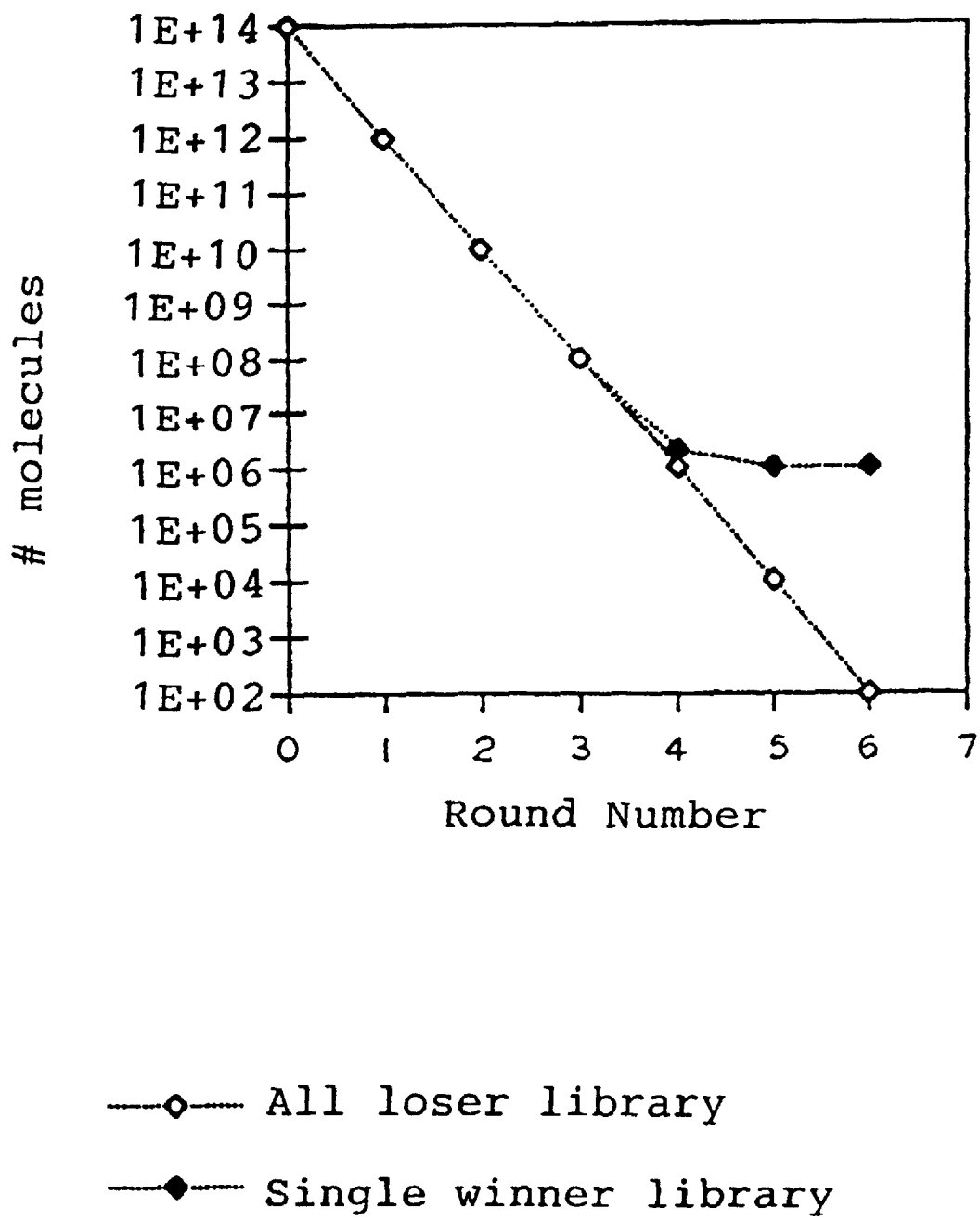
FIG. 3 graphically represents changes in recovery for each round in a reiterative process for a library containing "losers" and a library containing one "winner"

If a library contains one or more winners, under ideal conditions all winners will interact with the target at each iteration provided that the concentration of winners is less than the target concentration, and the target concentration is greater than the $K_d$ for its association with the winners. Thus, the proportion of winners to total compounds associated with target increases rapidly with each iteration of exposure to target. At some point in the reiteration process the proportion of winners to total compounds becomes great enough that winner compounds predominate in the population. Accordingly, in the semi-log plot, the curve visibly departs from linearity; ultimately, in an idealized situation, a plateau is reached and the same amount of compound is observed binding to target with further rounds of iteration. For example, an idealized binding experiment is shown in FIG. 2 in which a library contains $10^6$ copies of $10^8$ different nucleic acid sequences of which only one sequence is a winning sequence. By the fifth iteration, the curve departs visibly from linearity. FIG. 3 demonstrates a superimposition of the plots from FIGS. 1 and 2. By the fifth iteration 100 times more compound is recovered from a library containing a winner (hereinafter referred to as a "winner library") than from a library containing no winners (hereinafter a "loser library"); by the sixth iteration, 10,000 times more compound is recovered from a winner library than from a loser library.

Consider the case of a library that contains two compounds that can interact with target, such that compound A interacts with higher affinity for the target than compound B. If the assay is carried out such that the concentration of target is at or below the $K_d$ for binding to compound B but above the $K_d$ for binding to compound A, after several iterations, most of the observed interaction with target will be due to compound A. For example, if compound A interacts with target with twice the affinity of compound B, after 4 iterations, there is approximately $2^4$, or 16, times more compound A interacting with target than compound B. Similarly, if compound A interacts with target with three times the affinity of compound B, after 4 iterations, there is $3^4$, or 81, times more compound A recovered from the library than compound B. Thus, libraries are likely to be identified as "winner libraries" because of a single best member compound, unless they contain numerous compounds that interact with a target with very similar affinities.

Furthermore, for the same reasons, if two libraries are compared and library A contains a winner with just marginally higher affinity than any winners in library B, the library A will clearly be scored as a winner library relative to library B. This is important to the procedure because the ability to ascertain that a particular library contains winner(s) of higher affinity than other libraries will allow indirect elucidation of the winner(s) identity in the final screening steps of the overall procedure.

Figure 4:
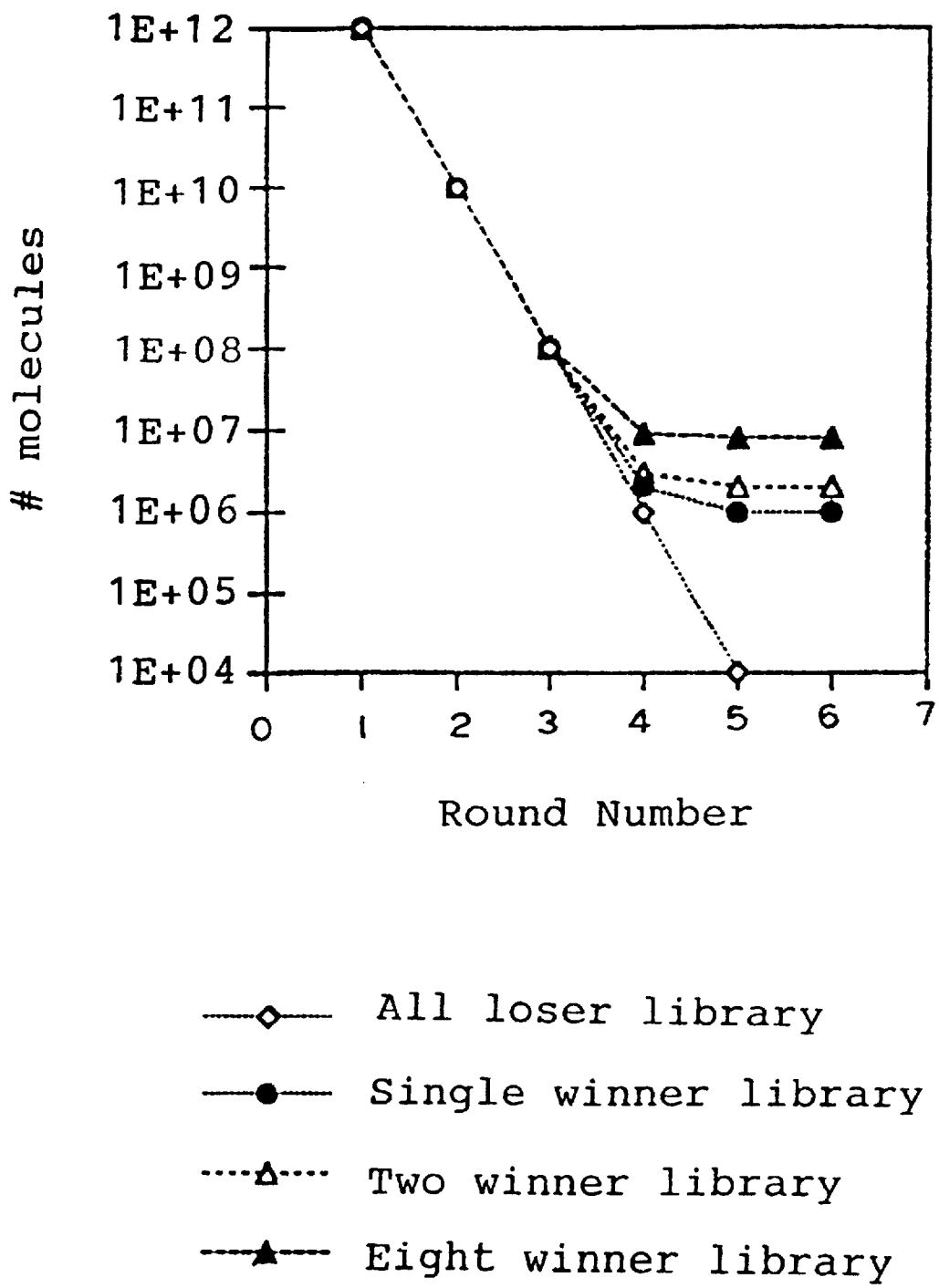
FIG. 4 graphically represents changes in recovery for each round in a reiterative process for different libraries.

If a library contains two winner compounds that interact with a target with the same high affinity, then the plateau level in the semi-log plot will be twice as high as the plateau level in a library containing only one winner (FIG. 4). Thus, under idealized conditions, one can not only distinguish a winner library from a loser library but also estimate whether there is more than one winner in a library.

Thus, as should be apparent, in accordance with the present invention, if a library contains no winners, a plot of the material recovered per round (or material eliminated per round) will be monotonic with ever decreasing amounts of material recovered each round, usually according to a relatively fixed percentage recovery (fixed percentage of elimination of losers) each round. A library containing one or more winners will follow the same plot until a round is reached where the winning compounds that are recovered at a higher percentage per round (eliminated at a lower percentage per round), become a majority of the remaining library mixture. In all subsequent rounds, the plot will reach a "plateau" because a relatively high recovery of material will be seen every round (a relatively low elimination of material in each round) once the majority of the remaining compounds are winners. Thus, by such a plot, the presence or absence of a winner in a library can be readily determined.

Although in accordance with one embodiment, the so-called elimination of losers is accomplished by recontacting of recovered compounds with the target in a reiterative procedure, the present invention also contemplates other methods for eliminating so-called losers in order to identify whether or not the library contains a winner.

Thus, for example, instead of recovering bound compounds and recontacting the target with the recovered compounds, after the initial binding, the target could be treated in any manner that would preferentially eliminate from the target those compounds that bound to the target at lower affinity. As a non-limiting example, this could be accomplished by a dialysis procedure in which a series of buffer (dialysate) changes into which the library is dialyzed would preferentially contain losers that cross the dialysis membrane whereas the target would continue to preferentially contact the winners that cannot cross the membrane while bound to the larger target. If, for example, the target-library incubation sample is placed in a dialysis chamber with a ten-fold excess of dialysate across a dialysis membrane that has a molecular weight cut-off such that a relatively large target could not cross the membrane but the relatively small library members can, then approximately 90% of the unbound library members will migrate across the dialysis membrane into the dialysate. Each time the dialysate is exchanged with fresh buffer, another 90% of the unbound members (losers) will migrate across the membrane, thereby lowering the total number of losers in the sample. The winners, in contrast, will be preferentially retained in the sample due to their interaction with the target.

The dialysate changes could even be achieved by a continuous flow of buffer into which the losers preferentially diffuse. After a period of time, the target-containing sample, or a portion thereof, could be assayed for the amount of library remaining. A library containing high affinity winners would retain more material after longer periods of time than a library with lower affinity compounds that would diffuse across the membrane at a much higher rate. Such a continuous time-based procedure is essentially a very rapid multi-round procedure wherein the rounds consist of the constantly "reset" initial dialysis condition as the dialysate is changed.

Another procedure for eliminating losers to thereby enrich winners after contact of a library with a target molecule which may be employed for screening a nucleic acid library involves the generation of "sense" and "antisense" strands from the nucleic acids that bound to the target molecule. Cycles of hybridization and melting of the strands, with elimination of those strands that do not hybridize, as described in U.S. patent Ser. No. 079,677, filed on Jun. 18, 1993 result in elimination of losers, and by using a plot as hereinabove described, there can be determined whether or not such library contains a winner sequence.

Thus, as should be apparent, any one of a wide variety of procedures that will eliminate the so-called losers at a rate greater that the elimination of winners will permit a determination of whether or not a library contains a winner in that the elimination of the losers will result in a rate of change with respect to recovery of the compounds which change in rate indicates that the library contains a winner.

Thus, in accordance with the present invention, a change in the rate of elimination of compounds that are bound to the target (or a change in the rate of recovery of compounds) indicates whether or not a winner is present in a library. Thus, for example, the rate can be a two-fold change or greater in the rate of recovery of compounds or in the rate of elimination of compounds. Thus, as should be apparent, the rate of elimination of compounds for the purposes of the present invention is related to the rate of recovery of compounds, and a change in the rate of either is indicative of the presence of a winner in a library.

In accordance with the present invention, one can calculate the initial size of a library (N=total number of molecules) required to screen for winners of a particular rarity, and the number of iterative rounds (R) required to detect a 100% increase in the number of remaining molecules in a winner library versus a loser library. A winner has an initial frequency (f) equal to the ratio of winners to losers in the library and can be recovered from each iteration with a certain percent yield (y). The losers are recovered with a certain background percentage (b). Let d=the smallest number of molecules that can be detected (by fluorescence or a variety of other methods). Then, the number of rounds required to result in a two-fold (or 100%) increase in the total molecule number remaining is defined by the equation $R=\log(f)/\log(b/y)$. And, the library must be of size $N=d/[(f)(y/100)^R]$ to have enough molecules left at round R to be above the detection threshold. For example, a reasonably large library in practice can contain about $N=10^{15}$ molecules (about 1 nanomole), with a detection threshold of about d=10,000 molecules, a background of b=0.1%, and a yield/iteration of winners of about y=20%. Given these parameters, these two equations can be solved together for R and f to show that about one winner in $10^8$ total molecules would be detectable after 4 rounds of selection as a 2-fold increase in the observed number of molecules recovered. These are reasonable numbers for an actual experiment, but are not necessarily limiting because detection threshold, background, initial library size, and yield of winners could all be even more advantageous in practice, allowing for even rarer winners to be detected. Note that in this example the library could contain $10^7$ copies of $10^8$ unique sequences and the procedure could detect one unique sequence that has the highest affinity for the target. Alternatively, the library could have as many as $10^{15}$ unique sequences and the procedure could detect a subset (or family) of sequences of which there are as few as $10^7$ in the library.

The compounds that are used in formulating a library which is tested in accordance with the present invention may be any one of a wide variety of compounds, particularly since in accordance with the present invention it is not required to amplify compounds that initially bind to a target molecule. Thus, for example, the library may be a nucleic acid library which may be formed from either single-stranded and/or double-stranded nucleic acids, and such single-stranded nucleic acids may be either DNA or RNA. Similarily, when employing nucleic acids or oligonucleotides, such nucleic acids may be modified or unmodified nucleic acids.

The term "nucleic acid" as used herein means that the nucleic acid may be a ribonucleic acid, i.e. an RNA; a deoxyribonucleic acid, i.e. a DNA; or a mixed ribonucleic/deoxyribonucleic acid; i.e., the nucleic acid may include ribose or deoxyribose sugars, 2'-O-methyl ribose or other 2' substituted or conjugated sugars, or a mixture of such sugars. Alternatively, the nucleic acid may include other 5-carbon or 6-carbon sugars, such as, for example, arabinose, xylose, glucose, galactose, or deoxy derivatives thereof or any mixture of sugars.

One or more of the phosphorus-containing moieties of the nucleic acids may be modified or unmodified. The phosphorus-containing moiety may be, for example, a phosphate, phosphonate, alkylphosphonate, aminoalkyl phosphonate, alkyl-thiophosphonate, phosphoramidate, phosphorodiamidate, phosphorothioate, phosphorodithioate, phosphorothionate, phosphorothiolate, phosphoramidothiolate or phosphorimidate. It is to be understood, however, that the scope of the present invention is not to be limited to any specific phosphorus moiety or moieties. Also, one or more phosphorus moieties may be modified with a cationic, anionic, or zwitterionic moiety. The nucleic acid may also contain one or more backbone linkages which do not contain phosphorus, such as carbonates, carboxymethyl esters, acetamidates, carbamates, acetals, and the like. The nucleic acids may also contain one or more backbone linkage of peptide nucleic acids (PNA). (Egholm et al., *J. Am. Chem. Soc.*, 114, 1895, (1992).

The nucleic acids also include any natural or unnatural, substituted or unsubstituted, purine or pyrimidine base. Such purine and pyrimidine bases include, but are not limited to, natural purines and pyrimidines such as adenine, cytosine, thymine, guanine, uracil, or other purines and pyrimidines, or analogs thereof, such as isocytosine, 6-methyluracil, 4,6-dihydroxypyrimidine, hypoxanthine, xanthine, 2,6-diaminopurine, 5-azacytosine, 5-methyl cytosine, 7-deaza-adenine, 7-deaza-guanine, and the like.

The nucleic acids may be modified such that at least one nucleotide unit of the nucleic acids may include a conjugate group. Such conjugate groups include, but are not limited to, (a) amino acids, including D-amino acids and L-amino acids; (b) peptides, polypeptides, and proteins; (c) dipeptide mimics; (d) sugars; (e) sugar phosphates; (f) neurotransmitters; (g) hormones; (h) poly (hydroxypropylmethacrylamide); (i) polyethylene imine; (j) dextrans; (k) polymaleic anhydride; (l) cyclodextrins; (m) starches; (n) steroids, including sterols such as, but not limited to, cholesterol; (o) acridine; (p) vitamins; and (q) polyalkylene glycols, such as polyethylene glycol. Such moieties may make the nucleic acids more resistant to degradation in cells and in the circulation, and/or make the nucleic acids more permeable to cells. The conjugate moiety may be attached to the 3' terminal nucleotide unit and/or the 5' terminal nucleotide unit and/or to an internal nucleotide unit(s), or conjugate moieties may be attached to two or more nucleotide units at the 3' end and/or the 5' end of the nucleic acid. In one embodiment, substituted nucleotide units may alternate with unsubstituted nucleotide units. In another embodiment, all of the nucleotide units are substituted with a conjugate moiety.

The conjugate moiety may be attached to the nucleic acid at the purine or pyrimidine base, at the phosphate group, or to the sugar. When the conjugate moiety is attached to the base, it is preferably attached at certain positions of the base, depending upon the base to which the moiety is attached. When the moiety is attached to adenine, it may be attached at the C2, N6, or C8 positions. When the moiety is attached to guanine, it may be attached at the N2 or C8 positions. When the moiety is attached to cytosine, it may be attached at the C5 or N4 positions. When the moiety is attached to thymine or uracil, it may be attached at the C5 position.

In one embodiment, the nucleic acid includes from about 5 to about 100 nucleotide units, preferably from about 8 to about 60 nucleotide units.

In yet another embodiment, the nucleic acid represents a portion of a larger molecule which contains non-nucleic acid components, such as, for example, peptides or proteins, or simple carbohydrates, and lipids.

The nucleic acids may be in the form of a single strand, a double strand, a stem-loop structure, a pseudoknot, or a closed, circular structure.

The nucleic acids may be synthesized by a variety of accepted means known to those skilled in the art. For example, the nucleic acids may be synthesized on an automated nucleic acid synthesizer. Alternatively, the nucleic acids may be synthesized enzymatically through the use of flanking or primer sequences at the 5' and 3' ends. In another alternative, the nucleic acids may be synthesized by solution phase chemistry. It is to be understood, however, that the scope of the present invention is not to be limited to any particular means of synthesis.

The compounds used in forming a library in accordance with the present invention may be peptides.

Alternatively, the compounds may be organic compounds, such as, for example, oligosaccharides, benzodiazepines, etc. The selection of a suitable type of compound for forming a library is deemed to be within the scope of those skilled in the art from the teachings herein.

Similarly, the target molecule may be any one of a wide variety of target molecules to which compounds in the library may bind. Although the preferred target molecule is a polypeptide or protein, the present invention is not limited to such targets.

Similarly, the library screened in accordance with the present invention may be comprised of mixed compounds. For example, the library compounds may be comprised of oligomers containing a mixture of amino acids and nucleotides. Thus, in accordance with the present invention, the library can be formed from any one of a wide variety of compounds, and can be screened by contacting the library with any one of a wide variety of target molecules. Also, in accordance with the present invention, there need only be in the library compounds that will bind to a target, with the screening being accomplished so as to effect binding to the target molecule of those compounds that have at least a specified activity.

Although in a preferred embodiment, such predetermined activity is defined in terms of compounds that bind to a target with at least a specified affinity (or $K_d$), the present invention also contemplates determining whether or not a library contains one or more compounds that bind to a target with a specified activity in which such activity is measured in terms of inactivating or activating a target molecule.

For example, if a compound binds to a site on the target in a way that blocks the activity of that target stoichiometrically, one can determine the presence of winners in the library by measuring the reduction of activity of the target. In this embodiment, the inhibitory activity of the library would be tested after each iteration under conditions where all starting libraries exhibit activity. As material is lost from each library, thereby lowering the total concentration of compounds in the inhibition assay, loser libraries will lose their inhibitory activity. Winner libraries, however, will maintain a level of inhibition as long as the initial winner concentration exceeds the $IC_{50}$ for that compound. For example, suppose that $IC_{50}$ of winners is 1 nanomolar, the library has a nonspecific $IC_{50}$ of 1 micromolar, and the initial library concentration is 100 micromolar. If the frequency of winners in the library is one per $10^4$ compounds, then after 2 rounds of selection recovering 50% of the winners and 1% of the losers each round, the losers would be present at a concentration of only 10 nanomolar, and would therefore exhibit no nonspecific inhibition. Libraries containing winners, however, would still contain 2.5 nanomolar winner and would inhibit >50% through at least 3 rounds. Note that without reiteration the winners would not be detectable because of the nonspecific inhibitory activity of the library as a whole. In general, if winners have an $IC_{50}$ x-fold lower than the losers but are rarer than 1:x in the library, then only a reiterative procedure will allow them to be identified.

It is not a prerequisite of this invention to determine the amount of recovered compound after each iteration, or to prepare a semi-log plot, although such evaluations are preferred. As a non-limiting example, a benzodiazepine library (Bunin & Ellman, J. Am. Chem. Soc. 114, 10997, 1992) is tested for the presence of winners by contacting the library compounds with a target, separating bound from non-bound compounds by any of a number of separation techniques based upon the difference in molecular weight of the unbound benzodiazepines vs. those bound to target, such techniques being well-known in the art, extracting bound benzodiazepines, contacting such extracted compounds with target once again and continuing such iterations for as many cycles as is desired or possible. After the last iteration, one quantitates the presence of extracted benzodiazepines, for example by accelerator mass spectroscopy (Vogel & Turteltaub, Trends Analyt. Chem. 11, 142, 1992). By running in parallel a sample of one or more benzodiazepines previously determined to be loser(s), one can establish background levels for such loser(s) and by comparison deduce whether the experimental library contains winners.

As should be apparent to those skilled in the art, the term "iteration" or "reiteration" is not limited to recontacting those compounds that originally become bound to the target with the target and such term broadly encompasses a variety of procedures for treating those compounds that bind to the target, some of which have at least the specified activity and some of which have less than the specified activity in such a manner that those compounds that bound to the target and did not have the specified activity would be eliminated at a faster rate than those compounds, if any, which bound to the target and had at least the specified activity. Thus, for example, such reiteration to eliminate at a faster rate compounds that do not have a specified activity may involve a series of rounds or steps in which the compounds that bind to the target are recovered and recontacted with the target or may involve procedures as hereinabove described, for example, dialysis or, in the case of nucleic acids or oligonucleotides, melting of sense and antisense strands of those nucleic acids that bind to the target molecule in a manner such that those having a lower binding affinity are eliminated at a faster rate.

The amount of material recovered in the reiterative procedure employed in the present invention may be determined in a wide variety of ways. Thus, for example, every member in a library can be radioactively labeled or tagged with a fluorescent dye. As a non-limiting example, a nucleic acid library is labeled with $^{32}P$ by enzymatic end-labeling techniques well known in the art. After each iteration the nucleic acids associated with the target are recovered and all or part of the recovered nucleic acids are measured for Cerenkov disintegrations. Since such determinations are carried out in a scintillation spectrometer without addition of fluor, the total amount of the evaluated sample is preserved for further iterations of exposure to target. The number of Cerenkov disintegrations measured at each iteration determines the feasibility of carrying out a further iteration. Another non-limiting example is a library containing compounds each of which is covalently attached to a defined nucleic acid sequence (a "tag sequence") such that the quantity of compounds can be measured by any of the methods known in the art that use hybridization of a nucleic acid probe to a target sequence, in this case the tag sequence.

Alternatively, as another non-limiting example of the instant invention, each member of a peptide library is labeled with a relatively small fluor such as fluorescein or rhodamine. After each iteration of exposure to target, the quantity of recovered peptides is measured with a fluorometer. Once again, all or part of the recovered peptide population can be used for a further iteration if it is determined that there is sufficient fluorescent material to permit another round of selection and quantitation.

The present invention is also directed to prescreening in order to determine whether or not certain types of compounds or a certain size of a compound may be best suited for interacting with a target molecule.

Thus, for example, in searching for a peptide-based therapeutic, it may be desirable to determine the smallest peptide that interacts with a target since larger compounds are more expensive to produce and could be less bioavailable.

Accordingly, one can generate peptide libraries of different sizes and determine whether any library contains a winner. Thus, for example, if libraries of dipeptides, tripeptides and tetrapeptides are determined not to contain winners whereas pentapeptide and hexapeptide libraries are determined to contain winners, subsequent determination of winner peptide sequences can be carried out with pentapeptide libraries since these libraries are determined to be the smallest molecular weight libraries containing winners. Alternatively, both the pentapeptide and hexapeptide libraries (but not smaller molecular weight libraries) can be further analyzed for winning sequences.

As another non-limiting example of the instant invention, single-stranded nucleic acids identified as interacting best with a target are often determined to assume discrete recognizable structures such as stem-loops or pseudoknots. These structures are often sequence-non-specific but are presumably essential for providing a scaffolding to present the selected sequence-specific region of the nucleic acid to the target in such as way as to optimize interaction. The need to have such structural properties in the selected nucleic acids essentially reduces the proportion of compounds in the population that are suitable candidates as winners. The end result is that much of the value of a library's complexity is lost and the number of cycles required to narrow down the population of nucleic acids to those that have appropriate scaffolding is unnecessarily great. The use of libraries in which the member nucleic acids are designed to possess such structures in fact optimizes the selection procedure.

Among structured nucleic acids that are observed, stem-loop, bubbled, pseudoknot and tetraplex structures are known. Since base sequence is for the most part irrelevant in the structured regions so long as base pairs are formed, for the instant invention nucleic acid libraries are designed with fixed-sequence base-paired regions. If it is predetermined that a library in which all nucleic acids possess a particular structure contains one or more winners, such a structured library would present the following advantages in determination of the winner sequence(s): (1) selection is completed with fewer selection cycles; (2) because structure is already integrated into the compound, more complexity is introduced into variable regions of the molecule without exceeding the sequence complexity that can be selected for; and (3) if the structure contains a random region of the minimally permitted size for a winner sequence, this prevents a winning sequence from occupying multiple registers of the random region in different winner molecules, i.e., this reduces the number of different winner compounds.

Structured nucleic acid libraries are generated with automated nucleic acid synthesizers by procedures well known in the art. Libraries can be generated to assume structures that include, but are not limited to, stem-loops, bubbles, pseudoknots or tetraplexes. Libraries can contain one or more of these structures. Structured libraries can contain, RNA, DNA, a mixture of the two, and/or compounds comprised of modified nucleotides.

Stem-loop structures are generated by constructing a molecule with complimentary ends that base-pair with adequate affinity to maintain a stem-loop conformation. A non-limiting example of a simple stem-loop structure might have the sequence $G_xN_yC_x$ wherein x is at least 2 up to 10 or more and $N_y$ represents the random loop sequence in which y can be at least 3 up to 20 or more. In such a library, each G in the $G_x$ region would be expected to pair with a corresponding C in the $C_x$ region to form the following structure (x=5, y=6 is shown as an example):

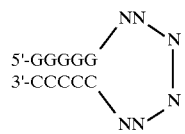

The loop can contain natural nucleotides (ribo A,C,G,U or deoxyribo A,C,G,T) or nucleotides modified in the base, sugar and/or backbone moiety. Examples of such modified bases include, but are not limited to, 5' methyl U, 2,6 diaminopurine, inosine. Examples of such modified sugars include, but are not limited to, 2' alkylated, 2'-O-alkyl, 2' halogenated, 2' amino substituted sugars. Examples of such modified backbone groups include, but are not limited to, phosphorothioates, phosphorodithioates, methylphosphonates, and amino alkyl backbones. The loop can also contain abasic-nucleotides or non-nucleotides, including, but not limited to, so-called PNAs, glycols or amino acids, or other monomeric units described hereinabove.

In the stem, the bases can be varied so long as they are configured to base-pair appropriately. In fact, it is preferable to vary the bases in the stem region to avoid slippage in base pairing: e.g., A can be substituted for G and T (or U) for C in the aforementioned structure or the stem can consist of a mixture of A-T (or A-U) and G-C base pairs. In addition, ribo G-U or modified ribo G-U base pairs can be used in the stem. Any modified bases are allowed in the stem so long as they form suitable base pairs. The stem can also contain occasional non-base-paired regions. The 3' or 5' end of the molecules (or both ends) can be attached to moieties that can be used for purposes of quantitation or identification. Examples of such moieties include, but are not limited to, unpaired nucleotides, biotin, fluorescein, amino acids, $^{32}$P. One or both ends of the stem can be covalently attached to an oligonucleotide "coding sequence" via an orthogonal compound as described by Beutel et al. (U.S. patent application Ser. No. 08/079,677) or to a tag sequence, as described above.

Bubbled structures are similar to stem loops except that stem regions surround the loop. A non-limiting way to generate a bubble library is by synthesis the following oligomers: $G_vN_wA_xM_yT_xN_zC_y$. In such structures, $G_v$ would base-pair with $C_y$ to form a stem on one side of the bubble and $A_x$ would base-pair with $T_x$ to form a stem on the other side of the bubble. The compounds in the libraries would then have the following structure (v=4, w=4, x=4, y=4, and z=4 is shown as an example):

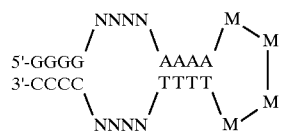

As envisaged, v can represent at least 2 up to 10 or more nucleotides and x can represent at least 2 up to 10 or more nucleotides. $N_w$ and $N_z$ together form the random loop structure, although $N_w$ or $N_z$ can have a fixed sequence. w and z can each be as small as one nucleotide up to 20 or more nucleotides. w and z can be equal or unequal.

The bubble libraries can contain naturally-occurring nucleotides or can contain modified nucleotides or non-nucleosidic components as described above for the stem-loop libraries. The molecules in the bubble libraries can contain adducts attached to the 3' or 5' end as described above for the stem-loop libraries.

Similarly, libraries can contain pseudoknot or tetraplex structures.

These and other structures used in libraries can be envisaged based on existing knowledge of such structures in the art (e.g., Puglisi et al., Acc. Chem. Res. 24, 152, 1991).

In addition to the foregoing, structural libraries can be constructed with compounds other than oligonucleotides, such compounds including, but not limited to, peptides and rigid organic compounds.

As one embodiment of the present invention, the pre-screen is used to determine both the nature and size of the structured nucleic acid that might best be tested for a given target. The procedure includes contacting the target with a series of libraries containing structured compounds that differ in the size of their random portion. As a non-limiting example, the target is contacted with stem-loop libraries containing progressively larger loops, such loops containing random nucleotide sequences. Thus, the different libraries can contain 4-nucleotide loops, 5-nucleotide loops, 6-nucleotide loops, etc., up to 20-nucleotide, or greater, loops. Following reiterative contact of the target with each of the stem-loop libraries, it is determined whether each of the libraries is a winner or loser library. If it is determined that winner libraries must contain a loop of at least a given size, then only structured libraries containing a loop size equal to, or larger than, that minimum size are used to identify the winner sequence(s).

It is a further aspect of the instant invention to test different structures for affinity to target. For example, a prescreen in accordance with the invention is carried out with stem-loop, bubble, pseudoknot, tetraplex and linear libraries, such that the molecular size of the compounds in each library is approximately the same. Libraries scored as winners are subsequently used for selection of optimal binding sequences as described below.

In yet another aspect of this invention, libraries are constructed that differ in net charge. For example, libraries can be constructed containing phosphorothioate backbones (Stein et al., Nucl. Acids Res. 16, 3209, 1988), methyl phosphonate backbones (Miller et al., U.S. Pat. No. 4,469, 863) or aminomethyl phosphonate backbones (Fathi et al., Bioconjugate Chem. 5, 47, 1994). In these libraries, the net charges will be negative, neutral or positive, respectively. Alternatively, the library components can contain nucleotides with a mixture of backbones so that the charge can be varied. By using the prescreen of the instant invention with these nucleic acid libraries, it can be determined which libraries contain winners. Prescreening can also be carried out with libraries varied with regard to both structure and charge.

In a very general embodiment, the present invention can be used with any polymeric or nonpolymeric library that can be synthesized in a stepwise manner (this is important for the winner identification described below) as long as the library members can be detected and quantitated by any means. There is no a priori reason for the libraries to be biopolymers such as nucleic acids, peptides, or derivatives and modifications thereof, though there are practical reasons for using these such as the convenient and widely practiced methods of synthesis known in the art.

In accordance with yet another aspect of the present invention there is provided a process for determining the identity or sequence of a compound that binds to a target molecule with at least the specified activity, wherein such sequence is determined indirectly, i.e., without actually having to sequence the compound. The present invention, in this aspect, is also directed to a wide variety of compounds of the type hereinabove described. Thus, for example, the compounds that may be employed in accordance with this aspect of the invention may be nucleic acids, or oligonucleotides, peptides, proteins, polymeric materials that are not naturally occurring, or organic compounds. The present invention, in this aspect, also does not require amplification, although it is possible when using nucleic acids to employ such amplification although it is not required in most aspects.

In accordance with this aspect of the present invention, there is prepared a plurality of individual sublibraries of the type of compound which is to be screened against a target molecule to ascertain the sequence of the compound or compounds that binds to the target molecule with at least the specified activity. In each of the sublibraries, the compounds therein have a known entity at a known position in the compound. Thereafter, each of the sublibraries is contacted with the target molecule to determine whether or not each of the sublibraries has a winner therein, i.e., a compound or compounds that bind to the target molecule with at least the specified activity. Based on the fact that for each of the sublibraries containing a winner compound or compounds, an entity of the compound is known and the position of the entity in the compound is known. Based on a determination of winner libraries there can be indirectly determined a compound(s) with a sequence(s) or structure(s) that will bind to the target molecule with at least the specified activity.

Thus, if for example, a prescreen of oligonucleotide libraries in a manner as hereinabove described determines that a 10 nucleotide random oligonucleotide library contains a winner sequence, then in accordance with this aspect of the present invention, 40 sublibraries would be synthesized, each containing one of the four nucleotides defined at one of the 10 positions. Each of the libraries would then be evaluated to determine, for example, in the manner hereinabove described, which of the libraries contained a winner sequence. Then the nucleotide sequence for a 10-nucleotide long oligonucleotide would be indirectly deduced by knowing the defined nucleotide at the defined position for each of the sublibraries that contained a winner.

For example, if the winner sequence was 5'-AGGCTATACG-3', the sublibraries $AN_9$, $NGN_8$, $N_2GN_7$, $N_3CN_6$, etc. would all have a plateau in their respective semi-log plots and be scored as positive, or as "winner libraries", whereas $CN_9$, $NAN_8$, $N_2TN_7$, $N_3GN_6$, etc. would be scored as negative, or "loser libraries". In total, 10 sublibraries corresponding to the 10 nucleotides in the winner sequence would be scored as positive whereas 30 libraries would be scored as negative.

Thus, in accordance with the present invention there is a combinatorial approach for identifying a sequence that binds to a target molecule with at least a specified activity. As hereinabove described, such activity may be a desired affinity, or may be a desired level of inhibition of activity of a target molecule, etc. Similarly, the compounds that are screened in a plurality of sublibraries may be any one of a wide variety of compounds such as, for example, oligonucleotides, peptides, polymers, organic compounds, etc. Although the invention is further described with respect to a nucleic acid that binds to a target with at least the specified activity, such description is equally applicable to other compounds, such as peptides and other organic compounds, and is equally applicable to definitions of activity other than affinity.

Thus, as a representative example, after determining that a single-stranded six-nucleotide oligonucleotide will bind to the target molecule with at least the specified activity, there are then prepared 24 sublibraries, each one fixed at one position with a known nucleotide. For example, if the sublibraries are constituted of natural ribonucleotides, the sublibrary set is the following, where N is a mixture of the four ribonucleotides:

ANNNNN NANNNN NNANNN NNNANN NNNNAN NNNNNA
CNNNNN NCNNNN NNCNNN NNNCNN NNNNCN NNNNNC
GNNNNN NGNNNN NNGNNN NNNGNN NNNNGN NNNNNG
UNNNNN NUNNNN NNUNNN NNNUNN NNNNUN NNNNNU

Each of the sublibraries is contacted with target and submitted to iterations of exposure to target, isolation and re-exposure to target, as described above, to determine whether the sublibrary contains one or more winners. By determining whether each sublibrary is a winner or loser library, a winner sequence can be deduced. For example, suppose that the reiterative described procedure of the invention is used to distinguish between winner and loser sublibraries within this set, and only the underlined sublibraries contain winners:

ANNNNN NANNNN NNANNN NNNANN NNNNAN NNNNNA
CNNNNN NCNNNN NNCNNN NNNCNN NNNNCN NNNNNC
GNNNNN NGNNNN NNGNNN NNNGNN NNNNGN NNNNNG
UNNNNN NUNNNN NNUNNN NNNUNN NNNNUN NNNNNU

In this instance, it can be deduced that the winner sequence is ACGCAC. For reasons mentioned above, a compound having as much as one-third the affinity of the winner compound acts, in effect, as a loser. Nevertheless, it is possible that a library contains a small number of compounds that have similar optimal affinities for a target. For example, there might be a consensus sequence in which some percentage of a winning sequence is critical in the interaction with target whereas other parts of the sequence are essentially irrelevant, serving as scaffolding. In such instances, there might be more than one winner sublibrary at a given fixed-base position, e.g.:

ANNNNN NANNNN NNANNN NNNANN NNNNAN NNNNNA
CNNNNN NCNNNN NNCNNN NNNCNN NNNNCN NNNNNC
GNNNNN NGNNNN NNGNNN NNNGNN NNNNGN NNNNNG
UNNNNN NUNNNN NNUNNN NNNUNN NNNNUN NNNNNU

In such an instance, it can be inferred that there is either a consensus sequence AYGYAR (i.e, ACGCAA, ACGCAG, ACGUAA, ACGUAG, AUGCAA, AUGCAG, AUGUAA and AUGUAG are all winners) (hereinafter Alternative 1), or a limited number of independent winner sequences, for example, ACGCAA and AUGUAG (hereafter Alternative 2).

It is possible to deduce which of the alternatives is likely to be correct through the quantitative analyses with the sublibraries. For example, if Alternative 1 is correct, the ANNNNN, NNGNNN and NNNNAN sublibraries all contain eight winner sequences, whereas if Alternative 2 is correct, the same sublibraries contain two winner sequences. Similarly, if Alternative 1 is correct, the NCNNNN, NUNNNN, NNNCNN, NNNUNN, NNNNNA and NNNNNG sublibraries each contain four winners whereas if Alternative 2 is correct, they contain one winner sequence. These kinds of differences in numbers of winners in the sublibraries are measurable as shown in FIG. 4, and could be used to deduce the correct alternative. In any event, since it is unlikely that a library will contain a large number of winners of unrelated sequence with very similar affinities for a target, it is a simple matter to synthesize the candidate winner sequences and test them individually for affinity.

Figure 5:
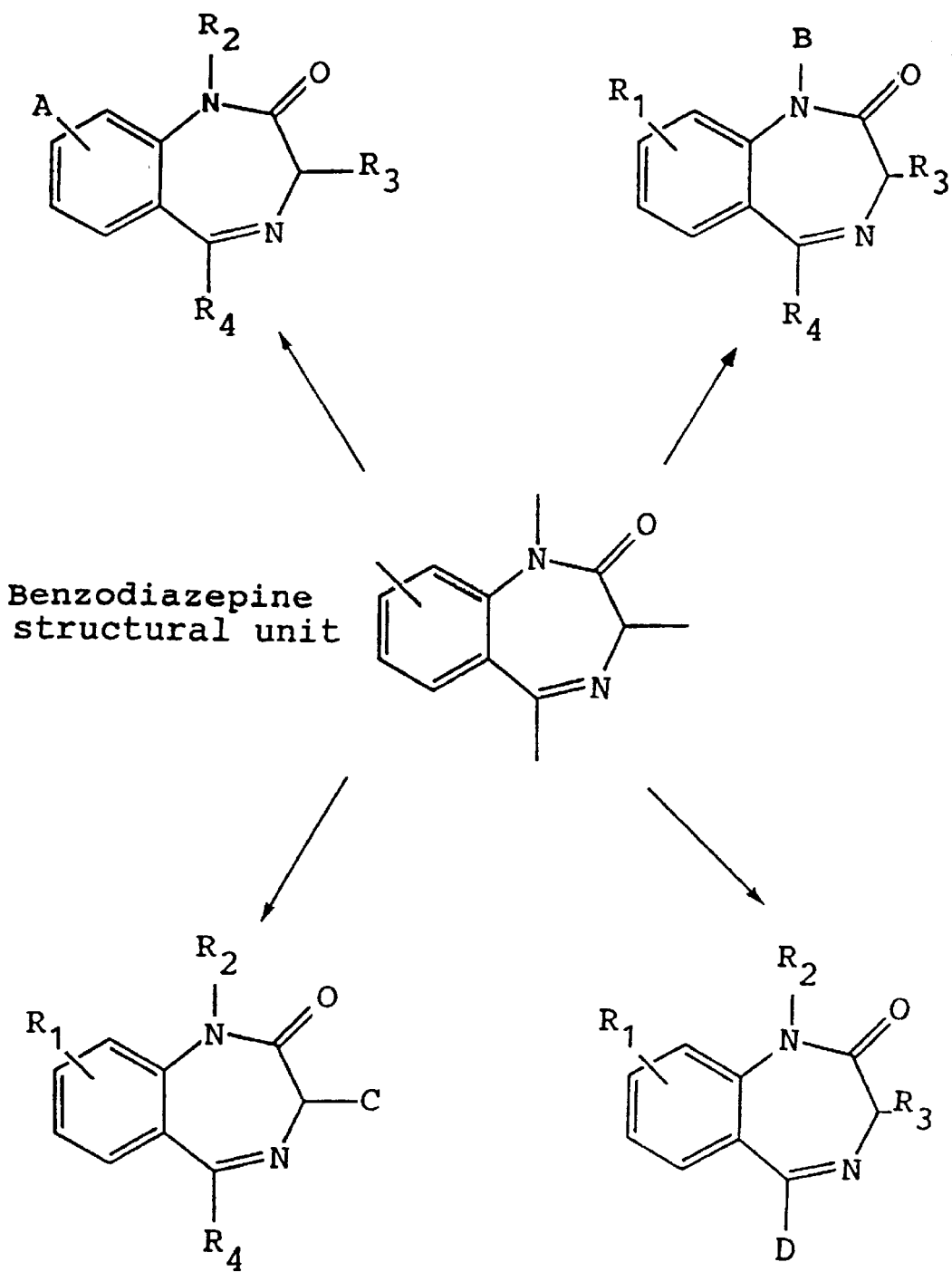
FIG. 5 depicts various benzodiazepine structures that might be used in formulating a library.

Whereas the above example of the invention is for identification of winner oligonucleotides, a broader embodiment of this invention is generalized to virtually any type of polymeric or non-polymeric compound library. For example, a large number of different benzodiazepine derivatives can be systematically synthesized such that they differ one from the other by substitution of chemical moieties present at various positions of the basic benzodiazepine structure, much as members of an oligonucleotide library differ in the nucleotide attached to each position of the polymer. By synthesizing sublibraries of benzodiazepines, each of which is characterized by having a fixed chemical moiety, at a particular position but a variety of different moieties at other positions (see, e.g., FIG. 5), one can test these libraries for winners and indirectly indentify the most active benzodiazepine derivative in a large library. The screening procedure with such libraries is analogous to the aforementioned analysis of oligonucleotide libraries wherein each sublibrary has a particular nucleotide defined at a particular position. In general, any library that can be systematically divided or synthesized as non-overlapping sublibraries, each of which has one distinct chemical characteristic at a particular site on the molecule, is amenable to the analysis of the invention.

Although the procedure of the instant invention does not require direct identification of a winner compound, the selection procedure can be coupled with direct identification. If the amount of material left after a given number of rounds is sufficient to allow identification using procedures well known in the art, such as DNA sequencing or cloning and sequencing for nucleic acid libraries, then such direct identification may be useful. This would only be the case if the winners are abundant enough and/or the library size is large enough to allow such direct identification without amplification of the material. In these cases, the method of the invention essentially serves as an indicator that a library contains winners and that the winners are abundant enough to identify directly. The winners can then either be identified via the indirect method or by direct procedures known in the art.

The invention will be further described with respect to the following examples; however, it is to be understood that the examples do not limit the scope of the invention:

EXAMPLES

Example 1

Identification of High Affinity Oligonucleotide Sequences

Six oligonucleotide libraries are compared to determine which, if any, of the libraries contains oligonucleotides that have a dissociation equilibrium constant of $K_d$=10 nM for binding to basic Fibroblast Growth Factor (bFGF). The libraries are:
1. Three "stem-loop" libraries, each with the sequence 5'-GGCCG($N_{5,7,9}$)CGGCC-3' such that one library contains 5 positions of randomized sequence, another contains 7 randomized positions, and another contains 9 randomized positions. Each of the three libraries contains the 10 nonrandom bases shown flanking the randomized region, five complementary bases on each side, so that the random region is located within a looped region of a stem-loop structure.
2. Three "bubble" libraries, each with the sequence 5'-GGCCG($N_{4,5,6}$)GACUGAAAACAGUC($N_4$)CGGCC-3' such that one library contains 4, another library 5, and another library 6 randomized positions across a bubble region from four (in all three libraries) additional randomized positions. Each of the three libraries contains 24 nonrandom bases as shown so that the random regions are located on each strand of a bubble in the center of a 10 base stem region with the loop sequence 'AAAA' at one end of the stem.

All six libraries are composed of 2'-OMe-RNA nucleotides at all nonrandom positions and contain 8 different nucleotides mixed in equal proportions in the randomized positions. The 8 nucleotides in the random positions are dA, dC, dG, dU, 2'-OMe-A ("A"), 2'-OMe-C ("C"), 2'-OMe-G ("G"), and 2'-OMe-U ("U"). Each library, therefore, contains $8^N$ unique members, so that, for example, the smallest library (the 5N loop library) contains $8^5$=32,768 oligonucleotides and the largest library (the 6+4N bubble library) contains $8^{10}$=1.07×10$^9$ oligonucleotides. In addition, all six libraries are synthesized so that a single fluorescein tag is at the 5' end of every molecule.

A total of $10^{15}$ molecules of each library are incubated for 30 minutes with bFGF in a 1 ml reaction of standard buffer (Tris-Cl pH 7.5, 150 mM NaCl, 3 mM MgCl$_2$) with 100 nM bFGF. Note that the $10^{15}$ molecules of library consist of approximately 3×10$^{10}$ copies of each of the 32,768 unique members of the 5N loop library, or approximately 10$^6$ copies of each of the 10$^9$ unique members of the 6+4N bubble library, and correspondingly different numbers of copies of unique members of each of the other libraries such that the total number is equal to $10^{15}$ in each case.

The six reactions are separately filtered through nitrocellulose filters (Millipore type HA) under vacuum and washed with 10 ml reaction buffer. The wet filters are then extracted with 200 ul 7M urea and 400 ul phenol, followed by a chloroform extraction, and the aqueous phase that contains the extracted oligonucleotides is collected. The oligonucleotides are then ethanol precipitated by standard methods and an aliquot of 1% of each sample is removed and measured by capillary electrophoresis with a fluoresence-detector to quantitate the total amount of fluorescent material in the sample from which the 1% was taken for measurement.

At this point, all six library samples have roughly $10^{13}$ molecules (observed as a fluorescent signal from the 1% aliquots equal to that of a $10^{11}$ molecule fluorescent standard), indicating that 99% of the compounds in each of the libraries has passed through the nitrocellulose filter and therefore that no more than 1% of each library is bound to the bFGF and thereby retained on the filter. This is consistent with none of the six libraries having an average library affinity for bFGF high enough to bind bFGF at a high percentage under these conditions.

The six samples collected after the first exposure to bFGF are then incubated once again under the same conditions with bFGF in new reactions with the addition of $10^{15}$ molecules of an unrelated non-fluorescent oligonucleotide sequence, 5'-AGTAGCTTGACGATCCG-3' that is added simply to be a "carrier" molecule to protect the library samples from being nonspecifically lost to test-tube surfaces. As before, the reactions are filtered and washed; the library samples are each extracted, precipitated, and quantitated by measurement of a 1% aliquot.

At this point (after two exposures to bFGF) approximately $10^{11}$ molecules remain in each of the six samples, indicating that once again the library samples have very little measurable binding to bFGF.

Two additional iterations of this procedure (incubation with bFGF, separation of bound molecules by filter, extraction, and measurement) result in ever decreasing numbers of molecules in each of the six samples, with approximately 99% of each library sample lost during each iteration. At this point (after a total of 4 iterations), each of the six samples is found to contain approximately $10^7$ molecules. After one more iteration, the 5+4N bubble library is found to contain nearly $10^7$ molecules, indicating that these remaining molecules, representing a rare subset of about one in $10^8$ molecules of this library, a level indicative of a single unique sequence in this library, has an affinity for bFGF high enough (i.e., a $K_d$ low enough) to bind to the 100 nM bFGF and be retained by the filter. The other five libraries all continue to decrease as in previous iterations so that each contains only about $10^5$ molecules after this fifth round. After yet another iteration, this result is confirmed because these other 5 libraries all decrease to about $10^3$ molecules and cannot even be measured by fluorescence detection while the 5+4N bubble library still has between $10^6$ and $10^7$ molecules.

From these results, the conclusion is reached that there is a bubble sequence in the 5+4N bubble library, as yet unidentified, that has very high affinity for bFGF; this sequence has higher affinity than any 5N loop, 7N loop, 9N loop, 4+4N bubble, or 6+4N bubble sequences in the other five libraries, and higher affinity than any of the other sequences in the 5+4N bubble library.

Based on this conclusion, 72 sublibraries are synthesized. Each sublibrary has the same 5+4N bubble fixed structural sequence. In the 9 bubble positions, however, only 8 of the positions are randomized while a single remaining position is specified as one of the 8 nucleotides (dA, dC, dG, dU, 2'OMe-A, etc.). There are 8 sublibraries, each with a different specified nucleotide, for each of 9 single specified positions, making a total of 8×9=72 sublibraries.

All 72 sublibraries and the original 5+4N bubble library (with all 9 positions randomized) are used exactly as described above in a reiterative procedure of incubation with bFGF, separation by filter, extraction, and measurement by aliquot. By the fifth and sixth iterations, only 9 sublibrary samples and the original library sample have greater than $10^5$ molecules. The 9 sublibrary samples each have 5–10 times more molecules than the reiterated original library sample. The 9 sublibraries that have samples with more molecules after the reiterations are:

5'-GGCCGANNNNGACUGAAAACAGUCNNNNCGGCC-3'

5'-GGCCGNUNNNGACUGAAAACAGUCNNNNCGGCC-3'

5'-GGCCGNNdANNGACUGAAAACAGUCNNNNCGGCC-3'

5'-GGCCGNNNdUNGACUGAAAACAGUCNNNNCGGCC-3'

5'-GGCCGNNNNAGACUGAAAACAGUCNNNNCGGCC-3'

5'-GGCCGNNNNNGACUGAAAACAGUCGNNNCGGCC-3'

5'-GGCCGNNNNNGACUGAAAACAGUCNdUNNCGGCC-3'

5'-GGCCGNNNNNGACUGAAAACAGUCNNGNCGGCC-3'

5'-GGCCGNNNNNGACUGAAAACAGUCNNNdCCGGCC-3'

From this information, it is deduced that the sequence of the high affinity 5+4 bubble sequence must be 5'-GGCCGAUdAdUAGACUGAAAACAGUCGdUGdCCGGCC-3', wherein the sequences from the experimentally randomized positions are underlined.

This sequence is synthesized and shown to have a $K_d$=10 nM for bFGF, which is consistent with its binding nearly quantitatively in the reiterative procedure that led to its identification when bFGF was 100 nM.

Example 2

Identification of High Affinity Peptide Sequences

Three peptide libraries are synthesized with lengths 4, 5, and 6 amino acids, respectively. Each has a single fluorescein moiety covalenty linked to the amino-terminus. Each of these libraries is incubated under standard buffer conditions with a particular antibody of interest. The incubations are in 1 ml of reaction buffer with $10^{15}$ molecules of peptide. After an initial 30 minute incubation, the reactions are transferred into a dialysis apparatus in which the 1 ml samples are separated from 10 ml of reaction buffer by a 5,000 molecular weight cut-off dialysis membrane. Unbound peptides (with molecular weights well below the dialysis cut-off) can freely diffuse through the membrane whereas antibody and antibody-bound peptides cannot. Because the volume of the dialysate is ten times larger than the sample volume, 90% of all unbound peptides (losers) migrate across the membrane, thereby preferentially decreasing the number of losers in the sample relative to the number of winners that are retained in the sample because they are bound to antibody. After dialysis for 15 minutes, 10 microliters of the reaction are sampled and measured for fluorescent intensity to determine the number of peptide molecules in the 1 ml reaction chamber. The dialysate is then removed and replaced with 10 ml buffer. This procedure of dialysis, removal of sample, and buffer exchange is repeated ten times.

The measurements indicate that the amount of 4 amino acid library in the reaction chamber decreases by a factor of 10 each time the 10 ml dialysate is exchanged.

The 5 and 6 amino acid libraries, however, decrease by a factor of 10 each time the dialysate is exchanged until the seventh round. Thereafter, more than half of the remaining peptides are retained in the reaction chamber during each buffer exchange. This indicates that very rare subsets of these libraries bind antibody with a high affinity such that they are unavailable for diffusion across the membrane. For the 5 amino acid library, this corresponds to only one unique peptide sequence. The 6 amino acid library contains 20 times more sequences with 20 times fewer copies of each, compared to the 5 amino acid library. Therefore, the fact that it shows the same dialysis behavior as the 5 amino acid library indicates that there are 20 peptides in it that bind with high affinity to the antibody.

Based on these data, the 5 amino acid library is used as the basis for synthesis and testing of 100 peptide sublibraries, using the same dialysis procedure. From the results of these experiments, the identity of the high affinity 5 amino acid peptide is deduced.

Numerous modifications and variations of the present invention are possible in light of the above teachings and, therefore, within the scope of the appended claims, the invention may be practiced otherwise than as particularly described.

What is claimed:

1. A process for identifying chemical entities at defined positions in a compound which binds to a target molecule with at least a predetermined binding affinity, comprising:

(a) contacting a plurality of individual libraries with a target molecule, wherein each individual library has a plurality of compounds having defined positions, with each compound of a library having the same defined chemical entity at the same one of the defined positions, and wherein the compounds of a library differ from the compounds of other libraries by at least one of the defined chemical entity or the defined position for a defined chemical entity, said compound being selected from the group consisting of polymers and nonpolymers, and said chemical entities at the defined positions for polymers being monomeric units and said chemical entities at the defined positions for nonpolymers being chemical substituents, said contacting being a repeated contacting under conditions to bind to the target molecule compounds in the library which bind to the target molecule with at least the predetermined binding affinity and to eliminate compounds that do not bind to the target molecule with at least the predetermined binding affinity;

(b) determining during said contacting the libraries in which there is at least one of (i) a decrease in the percentage of compounds in the remaining library that are eliminated or (ii) an increase in the percentage of compounds in the remaining library that are bound to the target molecule, and (c) based on the libraries determined in step (b) and based on the defined chemical entity at the defined position for each of the libraries determined in step (b), identifying chemical entities at defined positions for a compound which binds to the target molecule with at least the predetermined binding affinity.

2. The process of claim 1 wherein the repeated contacting is a reiterative procedure involving a plurality of rounds and the determining of step (b) is effected by determining the percentage of compounds in the library which bind to the target molecule in at least two of the rounds and comparing said percentages to determine whether there is an increase in the percentage of compounds in the remaining library that bind to the target molecule.

3. The process of claim 1 wherein the repeated contacting and eliminating is effected by dialysis.

4. The process of claim 1 wherein said target molecule is a protein.

5. The process of claim 1 wherein said repeated contacting comprises recovering compounds that bind to the target molecule and recontacting the recovered compounds with the target molecule.

6. The process of claim 1 wherein the compound is a polymer.

7. The process of claim 6 wherein the monomeric units are amino acids and the polymer is a peptide.

8. The process of claim 6 wherein the monomeric units are nucleotides and the polymer is an oligonucleotide.

9. The process of claim 8 wherein the oligonucleotide is a modified oligonucleotide.

10. The process of claim 1 wherein the compounds are labeled.

11. The process of claim 1 wherein in step (b) an increase in the percentage is determined by measuring at least twice during said repeated contacting the percentage of compounds present in the library which are bound to the target molecule and comparing said percentages.

12. The process of claim 1 wherein in step (b) a decrease in the percentage is determined by measuring at least twice during said repeated contacting, the percentage of compounds present in the remaining library which are eliminated and comparing said percentages.

* * * * *